(12) United States Patent
Bettinger

(10) Patent No.: US 6,539,250 B1
(45) Date of Patent: Mar. 25, 2003

(54) PROGRAMMABLE TRANSDERMAL THERAPEUTIC APPARATUS

(76) Inventor: David S. Bettinger, 8030 Coventry, Grosse Ile, MI (US) 48138-1119

(*) Notice: Subject to any disclaimer, the term of this patent is extended or adjusted under 35 U.S.C. 154(b) by 0 days.

(21) Appl. No.: 09/461,305

(22) Filed: Dec. 15, 1999

(51) Int. Cl.[7] .................................................. A61N 1/30
(52) U.S. Cl. ........................ 604/20; 604/501; 604/890.1
(58) Field of Search ................................ 604/590.1, 19, 604/20, 500, 21, 501, 22, 289, 290, 65–67, 246, 151, 131, 30, 31; 607/115, 149; 700/231, 240; 340/286.07

(56) References Cited

U.S. PATENT DOCUMENTS

| | | | | |
|---|---|---|---|---|
| 4,469,481 A | * | 9/1984 | Kobayashi .................... 604/67 |
| 5,169,384 A | * | 12/1992 | Bosniak et al. ................ 604/20 |
| 5,224,928 A | * | 7/1993 | Sibalis et al. .................. 604/20 |
| 5,368,562 A | * | 11/1994 | Blomquist et al. ............. 604/65 |
| 5,681,285 A | * | 10/1997 | Ford et al. ................... 604/151 |
| 5,850,344 A | * | 12/1998 | Conkright .................... 700/231 |
| 5,860,957 A | * | 1/1999 | Jacobsen et al. ............. 604/156 |
| 5,876,368 A | * | 3/1999 | Flower ........................ 604/20 |
| 5,935,099 A | * | 8/1999 | Peterson et al. ............... 604/65 |
| 5,980,934 A | * | 11/1999 | Reber et al. ................. 424/449 |
| 6,081,786 A | * | 6/2000 | Barry et al. .................... 705/3 |
| 6,161,095 A | * | 12/2000 | Brown ......................... 705/2 |
| 6,231,560 B1 | * | 5/2001 | Bui et al. .................... 604/500 |
| 6,270,455 B1 | * | 8/2001 | Brown ....................... 600/300 |

* cited by examiner

Primary Examiner—Brian L. Casler
Assistant Examiner—Jennifer Maynard

(57) ABSTRACT

A programmable transdermal therapeutic apparatus provides facile programming instruction means to query for a patient's attributes and to translate these attributes into customized patient limits and instructions of specific medication delivery regimens. More specifically, when the therapeutic apparatus is inserted into an active personal computer and the programming instruction means is uploaded, then the delivery regimen is downloaded into the dispensing device of the therapeutic apparatus. In its preferred embodiment, this transdermal therapeutic apparatus is configured as a floppy disk for its interactions with a personal computer.

8 Claims, 3 Drawing Sheets

PROGRAMMABLE TRANSDERMAL THERAPEUTIC APPARATUS

BACKGROUND OF THE INVENTION a) Field of the Invention

The present invention relates to a programmable system means for regulating the introduction and transdermal delivery of medicaments and therapeutics utilizing and integral to a microprocessor embedded dispenser. More particularly, the present invention relates to programmable system means embodied in the therapeutic apparatus which comprises a carrier unit, containing at least one microprocessor controlled transdermal dispenser, connected to a computer interface module embedded with appropriate software. The programming means specifically and uniquely provide patient customized limits and instructions for a removable dispenser with the ability to exist and function for patient use as a responsive entity after programming completion.

b) Description of the Prior Art

In the prior art of transdermal drug delivery, the common approach to regimen management was to manufacture differing packages that would vary the concentration and amount of a drug to control the dispensing rate and duration respectively. Thus the healthcare professional commonly selects a preset dispenser that most closely approximates the needs of an individual patient.

In the prior art of programmable control for transdermal drug applicator systems, Bettinger, U.S. Pat. No. 5,474,527, discloses a microchip controlled patch with a multiplicity of medicinal vials that can responsively vary the drug selection, the initiation and cessation of dispensing, and the drug concentration. Bettinger leaves the patient locked into a responsive but preset regimen suitable for a wide group of patients, but only approximate for the needs of an individual patient.

In the prior art of programmable control for transdermal drug applicator systems, Sibalis et al., U.S. Pat. No. 5,865,786, disclose a microprocessor controlled wrist band worn transdermal dispenser preset with programmed instructions. This wrist band dispenser is susceptible to connection with some undisclosed external preprogrammed system, prepared in a doctor's office, by means of the prongs of a plug. Neither the preprogrammed system components nor its functions are described or disclosed. This plug interface between the dispenser and the preprogrammed system is highly specific and non universal. The preprogrammed system of Sibalis severely limits the dispenser use for preset regimens for a broad class of patients, unsuitable for individual patient customization.

SUMMARY OF THE INVENTION

In order to overcome the above-mentioned deficiencies and problems in the prior art, this invention teaches a programmable transdermal therapeutic apparatus comprising:

1) a detachable microprocessor system controlled medication dispensing device attached to and in close proximity to,
2) a detachable computer interface module, compatible with a personal computer, and further containing and storing
3) a query and translator program selected to be descriptive of a multiplicity of beneficial therapeutic regimens of at least one medication contained within and actively disposed within the medication dispensing device.

Thus when this detachable computer interface module is inserted into an active personal computer and the program is uploaded, this program is selected to query for an individual patient's attributes, to translate the patient's attributes into customized limits and instructions of a specific medication delivery regimen, and to download the regimen into the dispensing device.

This programmable transdermal therapeutic apparatus may comprise a medication dispensing device which is attached to and in close proximity to a detachable carrier unit, where the carrier unit is attached to this detachable computer interface module.

More specifically, this invention teaches a programmable transdermal therapeutic apparatus comprising:

1. a detachable carrier unit possessing: a) at least one disposable, removable transdermal dispenser comprising: i. at least one beneficial fluid, and ii. an embedded microprocessor system providing the means for actuation, pre-selected timing, rate, cycles, and duration of dispensing the beneficial fluids, and iii. dispenser activation means, connected by appropriate wiring means to, iv. independent power supply means connected by appropriate wiring means to the microprocessor system, and b) an auxiliary battery backup, connected by appropriate detachable wiring means to the transdermal dispenser, and c) the carrier unit possessing appropriate coupling means on a first side, furthermore the coupling means for temporary connection to,
2. a detachable computer interface module possessing: a) a first side with appropriate matching coupling means for temporary connection to the carrier unit, and b) a second opposing side with appropriate coupling means for temporary connection of the apparatus to a personal computer during programming of the microprocessor, and c) an appropriate download-capture mechanism, connected by appropriate detachable data wiring means to the removable transdermal dispenser, and further connected by appropriate data transport means to second side computer coupling means.

The therapeutic apparatus when in temporary direct compatible interconnection with a standard access port of a personal computing device, running software designed to query, interpret, and program the micro-processor memory provides for predetermined timing, rate, cycles, and duration of dispensing upon dispenser activation.

The disposable transdermal dispenser component of the present invention is activated when the protective storage shield is removed. Additionally, this microprocessor controlled dispenser possesses programming memory to begin system timing at the removal of the protective storage shield. Furthermore, this programming memory deactivates the dispenser upon the expiration date of the medications and the completion of the patient specified regimen.

The detachable carrier unit possesses an internal auxiliary battery. This battery serves as a power source for power backup and management, as well as to maintain an active dispenser during programming.

The computer interface module component of the present invention temporarily connects the carrier unit containing disposable dispenser to a personal computer through a standard access port. This computer interface module possesses at least one personal computer program internally resident on common computer input/output media.

The software run by the personal computing device is selected to possess the ability to query the personal computing device for time zone and location of system use and also to query the original equipment manufacturer internet site for the most current programming instructions and application data.

The software run by the personal computing device is further selected to possess the ability to query the pharmaceutical manufacturer internet site for drug recall information and to screen for drug interactions, alerting the healthcare professional as required.

This invention teaches a programmable transdermal therapeutic apparatus comprising a detachable computer interface module further possessing: a) a display for exhibiting independent alphanumeric data, where this alphanumeric data is entered into this display with the use of and controlled by, b) a touchpad control containing multiple buttons selected for the ability to provide the functions of data display activation/deactivation, data category selection, and scrolling. Thus programming selection for an antidote based upon age, sex, weight, and particular chemical/biological hazard provides programming instruction to the dispenser of the therapeutic apparatus such that this antidote is administered to the patient upon dispenser activation.

The method of programming a transdermal dispenser of the present invention comprises the steps of:
1) booting up the personal computer,
2) inserting and connecting a computer interface module, connected by appropriate coupling means to a carrier unit conveying microprocessor controlled dispenser, to a personal computer,
3) permitting and commanding the personal computer software to recognize the presence of the microprocessor controlled dispenser,
4) permitting and commanding the personal computer software to query the health care professional, the personal computer, and the internet for patient and prescription data selected from a) the active medicinal agents of the prescription, b) sex, weight, and age of patient, c) special patient problems, d) time zone and location of system use, e) pharmaceutical recall information, and f) drug interaction data,
5) permitting personal computer software to interpret the data input of the healthcare professional,
6) permitting personal computer to utilize computer interface module to program the dispenser microprocessor memory by saving interpreted parameters to the microprocessor,
7) permitting personal computer software to record the prescription data,
8) permitting personal computer software program closing,
9) disconnecting the therapeutic apparatus from the personal computer and disconnecting the carrier unit from the computer interface module,
10) removing the microprocessor controlled dispenser from the carrier unit,
11) removing protective activation shield of the microprocessor controlled dispenser thereby activating the microprocessor controlled dispenser and attaching the microprocessor controlled dispenser to the skin at an appropriate location,
12) program dispensing by dispenser of at least one beneficial fluid during the prescribed dispensing duration,
13) removing microprocessor controlled dispenser at completion of the prescribed dispensing duration by the appropriate individual.

The present invention is a programmable therapeutic apparatus comprising
a) a microprocessor controlled medication dispensing transdermal device, including a patch, communicating by detachable means with
b) a carrier unit communicating by detachable means with
c) a removable computer interface module containing and storing for upload to and activation within a personal computing device a program comprising
   a first program component selected to be descriptive of a multiplicity of beneficial therapeutic regimens of at least one medication contained within and actively disposed within said transdermal device,
   a second program component selected to query for an individual patient's attributes
   a third program component selected to translate said patient's attributes into customized limits and instructions of a specific beneficial therapeutic regimen compatible with said attributes, and
   a fourth program component selected to download said regimen to
d) said carrier unit possessing means for programming of said transdermal device so as to dispense said regimen as an independent entity after programming completion, detachment of said patch from said carrier unit, and application.

1. Objects of the Invention

A general object of the present invention is to attain the means that provides for a programmable transdermal dispenser to exist and function on its own for patient use as a responsive and independent entity.

Another general object of the present invention is to readily achieve programmable system means in a facile manner providing for the programming of the dispenser via a computer interface by any healthcare professional using the ubiquitous personal computer.

An additional general object of the present invention is to readily achieve programmable system means to provide for variation in timing of the administration of medication. Medications may be administered on an hourly, daily, circadian rhythm, weekly, or any such appropriate basis as deemed necessary by the healthcare professional.

A still additional general object of the present invention is to readily achieve programmable system means to provide for exact control of variation in duration of the administration of medication. The duration of the administration of medication for the patient may be any such appropriate number of days as deemed necessary by the healthcare professional.

A still additional general object of the present invention is to readily achieve programmable system means to provide for instantaneous control of the variation in dispensing rate of medication due to the program and/or the sensors.

A still additional general object of the present invention is to readily achieve programmable system means to provide for a pre-programmed multi-drug regimen.

A still additional general object of the present invention is to readily achieve programmable system means to provide for the automatic dislodgment of the dispenser from the patient upon completion of the administration of medication.

A still additional general object of the present invention is to achieve facile programming selection, while the patch remains anchored in the therapeutic apparatus, of antidotes for exposure to hazardous chemical and biological agents.

2. Features of the Invention

In keeping with these objects and others which will become apparent hereinafter, one feature of the present invention resides, briefly stated, in the microprocessor controlled dispenser and its internal programming with the accompanying means for the selective dispensing of medications, on-command by program instruction, timing, rate, cycles, and duration.

Another feature of the present invention resides in the computer interface module or docking module which provides for programming the microprocessor controlled dispenser utilizing a personal computer with ease and great facility.

An additional feature of the present invention resides in the internal programming of the microprocessor controlled dispenser which insures greater drug efficacy due to expiration date dispenser deactivation.

A still additional feature of the present invention resides in the dispenser means for selective dispensing on-command by program instruction which prevents medication overdose because of predetermined timing, rate, cycles, and duration.

A still additional feature of the present invention resides in the precise dosage of medication by program to children based on weight rather than age criteria.

A still additional feature of the present invention resides in the touchpad control and display unit of the computer interface module which provides the means for facile programming selection of antidotes for hazardous agent exposure.

It will be known to one of ordinary skill in the art that the microprocessor controlled dispenser may display program input data.

It will be additionally known to one of ordinary skill in the art that the microprocessor controlled dispenser may possess either an ambient light sensor or a movement/activity sensor.

It will be further known to one of ordinary skill in the art that the microprocessor controlled dispenser may possess a temperature sensor. Dispensing would cease should the body temperature fall below a pre-set level so that that the adhesively attachable transdermal dispenser may be reattached to the patient if it becomes dislodged. The dispenser internal timing system would adjust accordingly.

It will be still further known to one of ordinary skill in the art that the carrier unit conditions electrical signals sent to the dispenser and vice versa. If the carrier unit is configured as a floppy disk, it may have its own separate power supply.

It will be still further known to one of ordinary skill in the art that the personal computer software feeds back the results of data input.

It will be still further known to one of ordinary skill in the art that the personal computer software requests approval of results.

It will be still further known to one of ordinary skill in the art that the personal computer software provides for the printing out and saving to a file of the healthcare provider's record.

It will be still further known to one of ordinary skill in the art that the internal programming of the microprocessor controlled dispenser has a unique serial number.

These and other modifications and applications of the present invention will become apparent to those skilled in the art in light of the following description of embodiments in this invention.

BRIEF DESCRIPTION OF THE DRAWINGS

The present invention is further described with reference to the accompanying drawings in which.

DETAILED DESCRIPTION OF THE DRAWINGS

Figure 1:
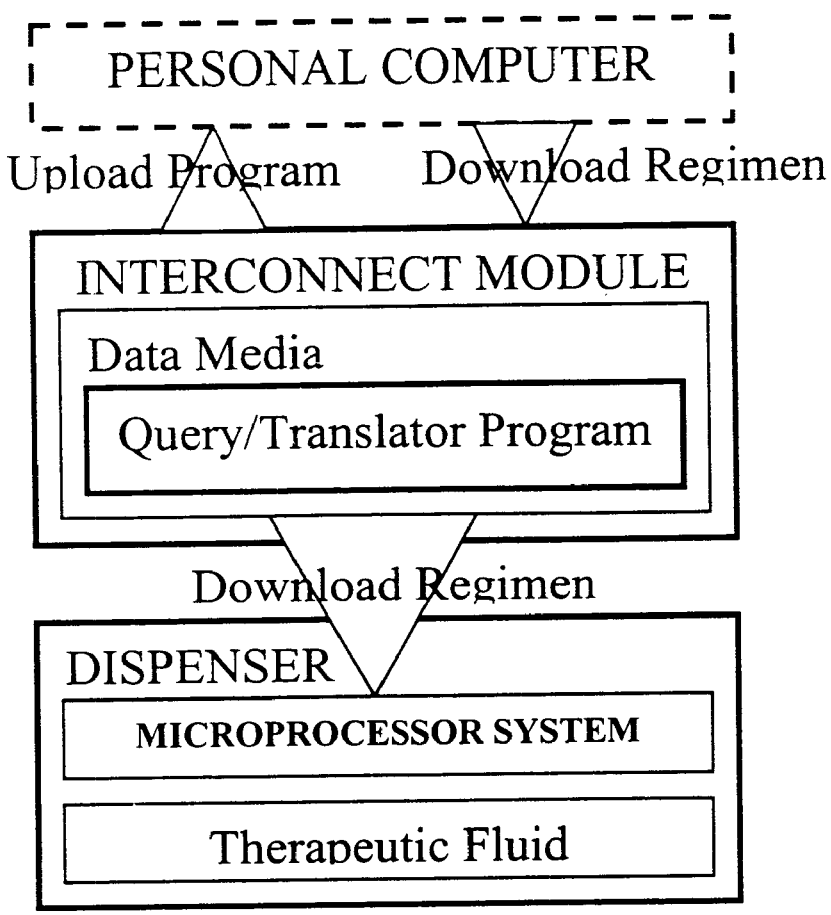
FIG. 1 is a schematic of the programmable transdermal therapeutic apparatus in general of the present invention showing the functional relationships among the components.

In FIG. 1 the therapeutic apparatus of the present invention comprises an interconnect module attached directly to the dispenser by means of a temporary and detachable coupling connection.

The interconnect module contains a query/translator program on the appropriate data media for upload to the personal computer, and a mechanism for accepting a download of regimen instructions from the personal computer and for transferring this download to the microprocessor of the dispenser. The computer interconnect module represents a common computer interface providing a detachable connection of the therapeutic apparatus to a personal computer.

Figure 2:
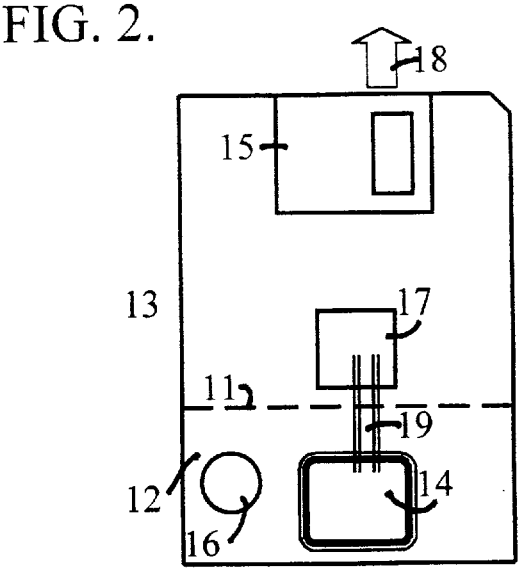
FIG. 2 is a drawing of the programmable transdermal therapeutic apparatus of the present invention in its preferred embodiment where the computer interface module is selected to be a floppy disk.

In FIG. 2 the programmable transdermal therapeutic apparatus comprises the carrier unit (12) with an embedded removal patch (14), and the computer interface module (13) configured as a floppy disk. The temporary connection of the carrier unit (12) with the computer interface module (13) is accomplished by means of a detachable coupling connection (11).

The embedded removal patch (14) of carrier unit (12) is connected by appropriate detachable electrical wiring means to an auxiliary battery (16) providing for facile disconnection when the patch (14) is removed from the carrier unit (12).

The computer interface module (13) possesses a floppy disk drive coupling connection (15) providing for temporary connection of the therapeutic apparatus to a personal computer. The direction of insertion (18) of the therapeutic apparatus into the personal computer floppy disk drive is indicated by the arrow. Data from the computer travels by appropriate data transport means, such as media dedicated tracks, to the download-capture mechanism (17). The data is then relayed by appropriate data wiring, such as a data buss (19), to the embedded patch (14) in the carrier unit (12).

Figure 3:
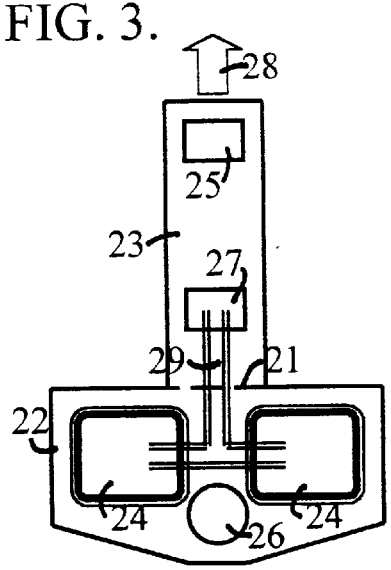
FIG. 3 is a drawing of the programmable transdermal therapeutic apparatus of the present invention in an embodiment where the computer interface module is selected to be a data strip.

In FIG. 3 the programmable transdermal therapeutic apparatus comprises the carrier unit (22) with an embedded removal patch (24), and the computer interface module (23) configured as a data strip. The temporary connection of the carrier unit (22) with the computer interface module (23) is accomplished by means of a detachable coupling connection (21).

The embedded removal patch (24) of carrier unit (22) is connected by appropriate detachable electrical wiring means to an auxiliary battery (26) providing for facile disconnection when the patch (24) is removed from the carrier unit (22).

The computer interface module (23) possesses a data strip data port coupling connection (25) providing for temporary connection of the therapeutic apparatus to a personal computer. The direction of insertion (28) of the therapeutic apparatus into the personal computer data strip data port is indicated by the arrow. Data from the computer travels by appropriate data transport means, such as dedicated media, to the download-capture mechanism (27). The data is then relayed by appropriate data wiring, such as a data buss (29), to the embedded patch (24) in the carrier unit (22).

Figure 4:
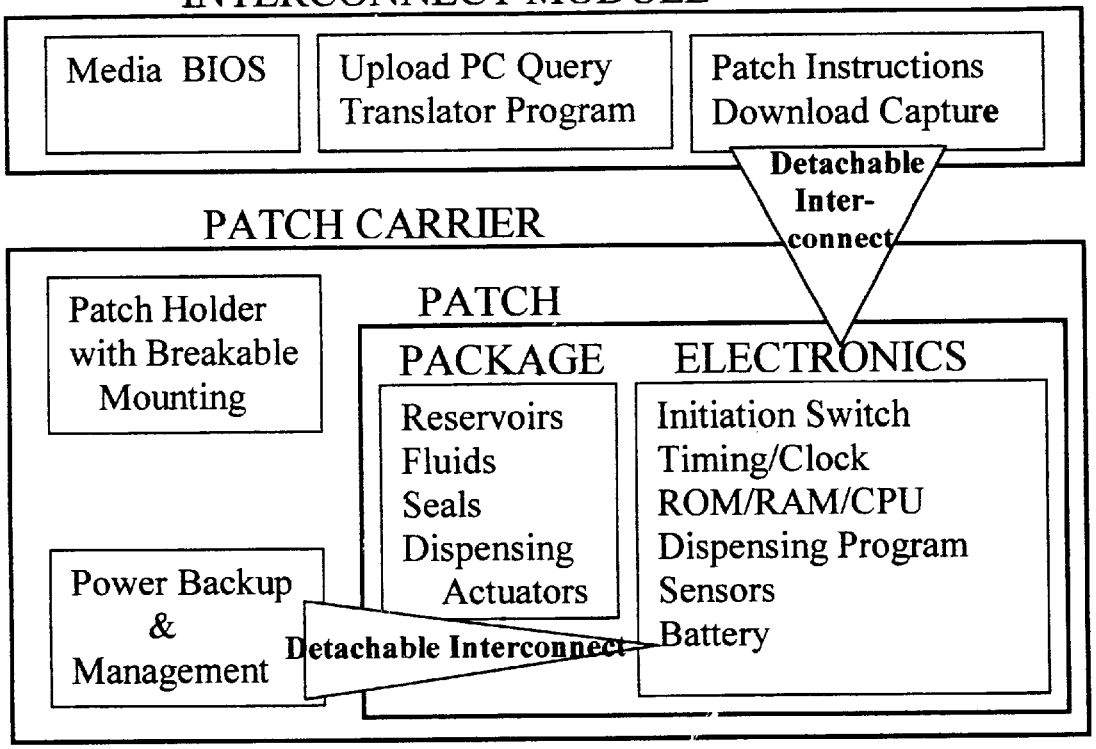
FIG. 4 is a schematic of a specific programmable transdermal therapeutic apparatus of the present invention showing the functional relationships among the components.

In FIG. 4 the therapeutic apparatus of the present invention comprises an interconnect module attached to the patch carrier by means of a temporary and detachable coupling connection or interconnect.

In general, computer media possess a basic input/output system as shown. The interconnect module of the present invention comprises this media BIOS, a mechanism for uploading query and translator programs to the personal computer, and a mechanism for downloading patch instructions to the patch.

The patch carrier comprises a patch holder with breakable and detachable mounting containing a removable patch, and additionally a power backup and management system. The patch itself comprises both a physical package and an electronics package. The physical package comprises the patch reservoirs, fluids, seals, and dispensing actuators. The electronics package comprises the initiation switch, timing/clock mechanism, ROM/RAM/CPU, the dispensing program, sensors, and patch battery. Instructions are transmitted through the download capture mechanism to the electronics package of the patch by means of temporary and detachable data wiring. The electronics package of the patch is further connected by temporary and detachable interconnect wiring to a power backup and management system.

Figure 5:
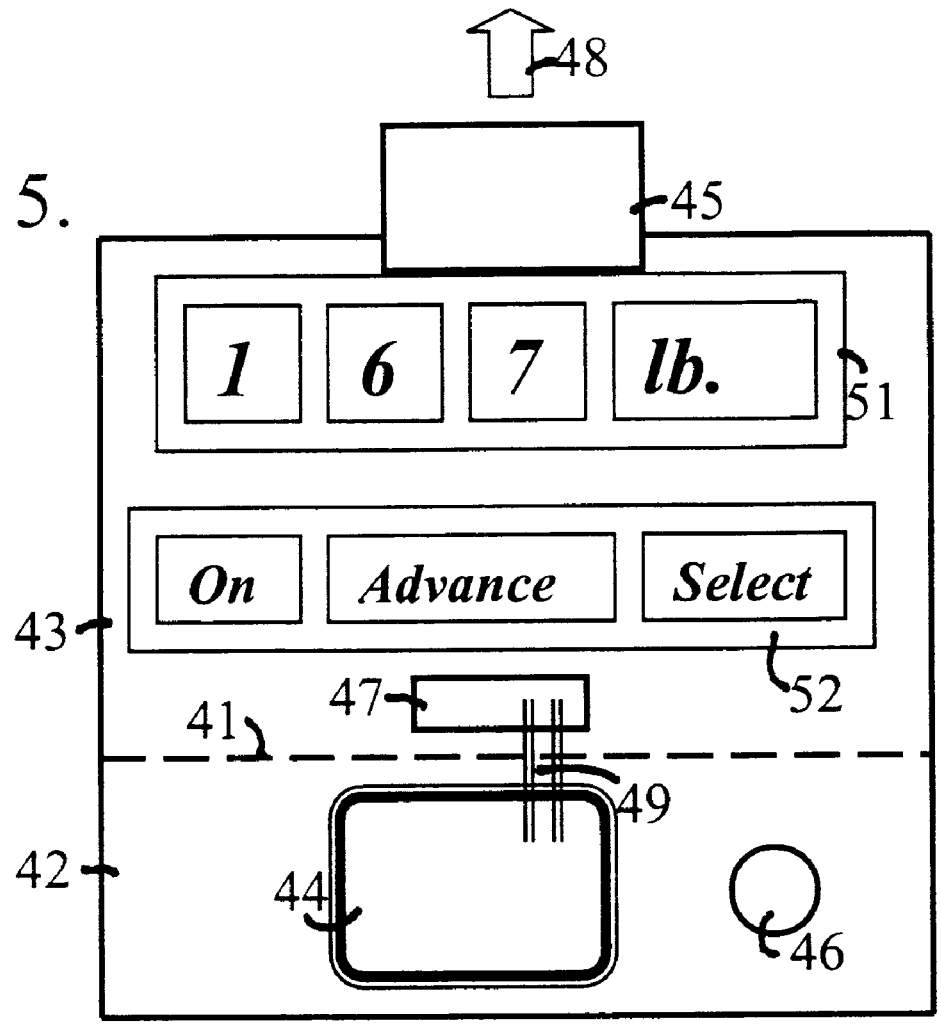
FIG. 5 is a drawing of the programmable transdermal therapeutic apparatus of the present invention in an embodiment where the computer interface module possesses a display and touchpad control.

In FIG. 5 the detachable computer interface module (43) further possesses a display (51) for exhibiting independent alphanumeric data. This alphanumeric data is entered into this display (51) with the use of and controlled by, a touchpad control (52) containing multiple buttons selected for the ability to provide the functions of data display activation/deactivation, data category selection, and scrolling. Programming selection for an antidote is based, upon age, sex, weight, and particular chemical/biological hazard which provides programming instruction to the download-capture mechanism (47). The On button serves to activate/deactivate the data display. Pressing the button once turns the display on and pressing a second time turns the display off. The Select button provides sequential access to the categories of age, sex, weight, and particular hazard. Pressing the Select button once brings up a particular category. The Advance button serves to provide movement through the display menu. Pressing the Advance button permits one to scroll the options available for each category. Once the option has been selected, one presses the Select button to enter that option in the display. One presses the Select button again to bring up another category. Pressing the Advance button permits one to again scroll the options available for this other category. The procedure is repeated until program selection is completed. This data is then relayed across the temporary detachable coupling connection (41) by appropriate data buss wiring (49), to the embedded patch (44) in the carrier unit (42).

The direction of insertion (48) of the therapeutic apparatus into the personal computer floppy disk drive is indicated by the arrow. Programming instruction from the personal computer is transmitted through the floppy disk drive coupling connection (45) to the download-capture mechanism (47) by means of dedicated media tracks. The data is then similarly relayed across the temporary detachable coupling connection (41) by appropriate data buss wiring (49), to the embedded patch (44). The embedded removal patch (44) of carrier unit (42) is additionally connected by appropriate detachable electrical wiring means to an auxiliary battery (46) for maintaining an active dispenser (44) during programming.

DESCRIPTION OF THE PREFERRED EMBODIMENT

A Programmable Transdermal Therapeutic Apparatus Configured as a Floppy Disk In its preferred embodiment the present invention is a programmable transdermal therapeutic apparatus configured as a 3.5" computer floppy disk.

The carrier unit possesses dimensions of approximately 2.0 inches by 3.5 inches, with a thickness of 3.0 mm. On its first side the carrier unit possesses an appropriate coupling connector for temporary connection to the computer interface module. Such appropriate connectors include lock and key, multi-pin, or snap connectors. The preferred coupling connector is multi-pin.

The carrier unit possesses at least one disposable transdermal dispenser. The dispenser may be of the nature of a patch, pad, shield, multi-needle injector, needleless hypodermic injector, or another appropriate type of dispenser. In its preferred embodiment the carrier unit possesses one dispenser; the preferred dispenser being a transdermal patch.

The dispenser activation means may be due to pre-programmed time/date information entered in the microprocessor memory by the healthcare professional, or may be due to individual actions of the patient when personally applying the patch. The preferred dispenser activation means is initiated when the patient personally removes the protective storage shield to activate the dispenser.

The independent power supply means consists of some type of chemical storage battery. Alkaline, NiCad, NiMH, and other such appropriate batteries are utilized as the power supply means. The preferred power supply means is the alkaline battery.

The power supply means is connected to the dispenser activation means, to the microprocessor, and to the download-capture mechanism (detachable wiring) by creating an electrical circuit with appropriate small gauge wiring.

The detachable computer interface module possesses dimensions of approximately 1.5 inches-by 3.5 inches, with a thickness of 3.0 mm. It possesses a first side with the appropriate matching multi-pin coupling connector for temporary connection to the carrier unit. A second opposing side with an appropriate disk access slot coupling connector provides for temporary connection to a personal computer by means of a floppy disk drive. The interface module possesses appropriate data media connecting the first side multi-pin coupling connector to the second opposing side disk access slot coupling connector. Thus when the therapeutic apparatus is in the floppy disk drive, the dispenser programming and operating instructions are transmitted from the personal computer through the media dedicated tracks of the interconnect module to the download-capture mechanism. In the preferred embodiment this download-capture mechanism comprises a disk drive head, powered by a battery, for reading and subsequently transmitting the magnetic data via the data buss to the microprocessor of the dispenser.

DESCRIPTION OF OTHER EMBODIMENTS

A Programmable Transdermal Therapeutic Apparatus Configured as a Data Strip

In the data storage arena smaller data media forms are emerging which will be common to all computers and offer a more efficient alternative to the floppy disk. The programmable transdermal therapeutic apparatus of the present invention may be configured in another embodiment as a magnetic strip card or as a data strip. There are over twenty readers for these data media forms listed in the Electronic Engineers Master Catalog (EEM 2000, D-191).

The carrier unit is configured as a magnetic strip card or as a data strip, with a width of 18–35 mm and a thick-ness of less than 3 mm. On its first side the carrier unit possesses a multi-wire coupling connector for temporary connection to the computer interface module.

The carrier unit possesses two disposable dispensers. In this particular embodiment the two carrier unit dispensers are transdermal patches.

The dispenser activation means of this particular embodiment is initiated when the patient personally removes the protective storage shield to activate the dispenser.

The independent power supply means of this particular embodiment consists of a NiMH chemical storage battery.

The power supply means is connected to the dispenser activation means, to the microprocessor, and to the download-capture mechanism (detachable wiring) by creating an electrical circuit with appropriate small gauge wiring.

The detachable computer interface module is also configured as a magnetic strip card or as a data strip with a thickness so as to achieve compatibility with the carrier unit. It possesses a first side with the appropriate matching multi-wire coupling connector for temporary connection to the carrier unit. A second opposing side with an appropriate data strip data port coupling connector provides for temporary connection to a personal computer by means of a PC data port. The interface module possesses appropriate dedicated media connecting the data strip data port coupling connector to the data strip download-capture mechanism. This download-capture mechanism, powered by a battery, reads and subsequently transmits the magnetic data via the data buss to the microprocessors of the embedded removal patches of the carrier unit.

Thus when the therapeutic apparatus is directly connected to the data strip data port connector of the personal computer, the dispenser programming and operating instructions are transmitted from the personal computer to the microprocessors embedded in the transdermal patches.

Numerous alterations of the programmable transdermal therapeutic apparatus herein disclosed will suggest themselves to those skilled in the art. However, it is to be understood that the present disclosure which relates to the preferred embodiment of the present invention is for purposes of illustration only and not to be construed as a limitation of the present invention. All such modifications which do not depart from the spirit of the invention are intended to be included within the scope of the appended claims.

What is claimed is:

1. A programmable therapeutic apparatus comprising
   a) a microprocessor controlled medication dispensing transdermal device, including a patch, communicating by detachable means with
   b) a carrier unit communicating by detachable means with
   c) a removable computer interface module containing and storing for upload to and activation within a personal computing device a program comprising
      a first program component selected to be descriptive of a multiplicity of beneficial therapeutic regimens of at least one medication contained within and actively disposed within said transdermal device,
      a second program component selected to query for an individual patient's attributes
      a third program component selected to translate said patient's attributes into customized limits and instructions of a specific beneficial therapeutic regimen compatible with said attributes, and
      a fourth program component selected to download said regimen to
   d) said carrier unit possessing means for programming of said transdermal device so as to dispense said regimen as an independent entity after programming completion, detachment or said patch from said carrier unit, and application.

2. The programmable therapeutic apparatus of claim 1, wherein said transdermal device possesses a protective storage shield selected to activate said beneficial therapeutic regimen upon removal from said transdermal device.

3. The programmable therapeutic apparatus of claim 1, wherein said transdermal device is selected to deactivate upon the expiration date of said at least one medication and the completion of said specific beneficial therapeutic regimen.

4. The programmable therapeutic apparatus of claim 1, wherein said program possesses a fourth program component selected to possess the ability to query after upload said personal computing device for the time and location.

5. The programmable therapeutic apparatus of claim 1, wherein said program possesses a fifth program component selected to query after upload the original equipment manufacturer internet site for the most current programming instructions and application data.

6. The programmable therapeutic apparatus of claim 1, wherein said program possesses a sixth program component selected to query after upload the pharmaceutical manufacturer internet site for the most current information concerning said medication contained and actively disposed within said transdermal device.

7. The programmable therapeutic apparatus of claim 1, wherein said carrier unit possesses a touchpad and a display for entering and exhibiting alphanumeric data.

8. The method of programming and application of a programmable therapeutic apparatus comprising the steps of
   1) booting up a personal computer;
   2) inserting and connecting a removable computer interface module communicating by detachable means with a carrier unit communicating by detachable means and conveying a microprocessor controlled medication device;
   3) permitting and commanding said personal computer to recognize the presence of, upload and activate a program stored on said removable computer interface module;
   4) permitting and commanding said program to query the healthcare professional, said personal computer, and the internet for patient, time, current dispenser, and current pharmaceutical data;
   5) permitting said program to interpret said data, and select a specific beneficial therapeutic regimen compatible with said data;
   6) permitting said program to download said specific beneficial therapeutic regimen to means for programming of said microprocessor controlled medication dispensing device;

7) permitting said program to record and store said pharmaceutical data within said personal computer;

8) permitting said personal computer to close said program;

9) removing said programmable therapeutic apparatus from said personal computer and detaching said removable computer interface module from said carrier unit;

10) detaching said microprocessor controlled medication dispensing device from said carrier unit;

11) removing a protective storage shield from said microprocessor controlled medication dispensing device thereby activating said microprocessor controlled medication dispensing device and attaching said microprocessor controlled medication dispensing device to the patient;

12) permitting said microprocessor controlled medication dispensing device to follow said specific beneficial therapeutic regimen for dispensing to said patient of at least one medication; and 13) removing said microprocessor controlled medication dispensing device from said patient at completion of said specific beneficial therapeutic regimen.

* * * * *